United States Patent
Laugesen et al.

(10) Patent No.: US 11,606,653 B2
(45) Date of Patent: *Mar. 14, 2023

(54) SYSTEM AND METHOD FOR VALIDATION OF HEARING AIDS FOR INFANTS USING A SPEECH SIGNAL

(71) Applicant: INTERACOUSTICS A/S, Middelfart (DK)

(72) Inventors: Søren Laugesen, Middelfart (DK); Bue Kristensen, Middelfart (DK)

(73) Assignee: Interacoustics A/S, Middelfart (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,848

(22) Filed: Mar. 21, 2022

(65) Prior Publication Data
US 2022/0272468 A1 Aug. 25, 2022

Related U.S. Application Data

(63) Continuation of application No. 16/457,364, filed on Jun. 28, 2019, now Pat. No. 11,310,612.

(30) Foreign Application Priority Data

Jun. 29, 2018 (EP) .................................... 18180836

(51) Int. Cl.
*H04R 25/00* (2006.01)
*A61B 5/12* (2006.01)
(Continued)

(52) U.S. Cl.
CPC ............. *H04R 25/70* (2013.01); *A61B 5/125* (2013.01); *A61B 5/38* (2021.01); *A61B 5/6814* (2013.01); *H04R 3/04* (2013.01); *H04R 25/55* (2013.01)

(58) Field of Classification Search
CPC ....... A61B 5/0006; A61B 5/121; A61B 5/123; A61B 5/125; A61B 5/291; A61B 5/369;
(Continued)

(56) References Cited

U.S. PATENT DOCUMENTS

| 5,291,785 A | 3/1994 | Downs |
| 6,868,345 B1 * | 3/2005 | Jensen ..................... A61B 5/38 |
| | | 702/31 |

(Continued)

FOREIGN PATENT DOCUMENTS

| CN | 105323690 A | 2/2016 |
| EP | 3 281 585 A1 | 2/2018 |

(Continued)

OTHER PUBLICATIONS

Anderson et al. "The Potential Role of the cABR in Assessment and Management of Hearing Impairment", Hindawi Publishing Corporation, International Journal of Otolaryngology, vol. 2013, Article ID 604729, 10 pages (Year: 2013).

(Continued)

*Primary Examiner* — David L Singer
(74) *Attorney, Agent, or Firm* — Birch, Stewart, Kolasch & Birch, LLP

(57) ABSTRACT

A system for validation of a hearing aid performance, especially in small children is disclosed. The validation of the performance of hearing aids after having being fitted to a small child who is not able to subjectively provide responses to sounds presented to the child via the hearing aids, is instead done in an objective manner, by using a naturally occurring signal, which has been modulated in order to create an ASSR evoking speech stimulus which is not considered as noise by a hearing aid.

21 Claims, 8 Drawing Sheets

(51) Int. Cl.
*A61B 5/00* (2006.01)
*H04R 3/04* (2006.01)
*A61B 5/38* (2021.01)

(58) Field of Classification Search
CPC ....... A61B 5/38; A61B 5/4851; A61B 5/6814; A61N 1/36039; H04R 2225/43; H04R 2225/81; H04R 25/55; H04R 25/70; H04R 3/04
See application file for complete search history.

(56) References Cited

U.S. PATENT DOCUMENTS

| | | | |
|---|---|---|---|
| 8,712,514 | B2 | 4/2014 | Nicol et al. |
| 2001/0034493 | A1 | 10/2001 | Stone et al. |
| 2001/0049480 | A1 | 12/2001 | John et al. |
| 2004/0064066 | A1 | 4/2004 | John et al. |
| 2004/0204659 | A1* | 10/2004 | John ............... A61B 5/38 600/559 |
| 2010/0076339 | A1 | 3/2010 | Marcoux |
| 2011/0295166 | A1 | 12/2011 | Dalton |
| 2011/0301486 | A1 | 12/2011 | Van Hek et al. |
| 2011/0313309 | A1 | 12/2011 | Nicol et al. |
| 2012/0059274 | A1 | 3/2012 | Zoth et al. |
| 2012/0197153 | A1 | 8/2012 | Kraus et al. |
| 2013/0101128 | A1 | 4/2013 | Lunner et al. |
| 2015/0350794 | A1 | 12/2015 | Pontoppidan |
| 2016/0235328 | A1 | 8/2016 | Elberling et al. |
| 2016/0262651 | A1 | 9/2016 | Thai-Van et al. |
| 2017/0196519 | A1 | 7/2017 | Miller et al. |
| 2018/0050202 | A1 | 2/2018 | Busby |

FOREIGN PATENT DOCUMENTS

| | | |
|---|---|---|
| JP | 2005-296607 A | 10/2005 |
| RU | 2002-125505 A | 3/2004 |
| WO | WO 2008/116462 A1 | 10/2008 |

OTHER PUBLICATIONS

Dajani, et al. "Improving Hearing Aid Fitting Using the Speech-evoked Auditory Brainstem Response", 35th Annual International Conference of the Ieee EMBS, Osaka, Japan, Jul. 3-7, 2013 (Year: 2013).

Glista et al. "A Pilot Study on Cortical Auditory Evoked Potentials in Children: Aided CAEPs Reflect Improved High-Frequency Audibility with Frequency Compression Hearing Aid Technology", Hindawi Publishing Corporation, International Journal of Otolaryngology, vol. 2012, Article ID 982894, 12 pages (Year 2012).

Reichenbach et al., "The Auditory-Brainstem Response to Continuous, Non-repetitive Speech Is Modulated by the Speech Envelope and Reflects Speech Processing", Frontiers in Computational Neuroscience May 1, 2016, vol. 10, Article 47 (Year: 2016).

Search Report issued in European priority application 18180836, dated Nov. 20, 2018.

Vijayalakshmi et al., "Electroacoustic Comparison of Hearing Aid Output of Phonemes in Running Speech versus Isolation: Implications for Aided Cortical Auditory Evoked Potentials Testing"., JInternational Journal of Otolaryngology, vol. 56, No. 4, 11 pages, Nov. 28, 2012.

Office Action dated Sep. 6, 2022 in corresponding Chinese Application No. 201910580596.X.

* cited by examiner

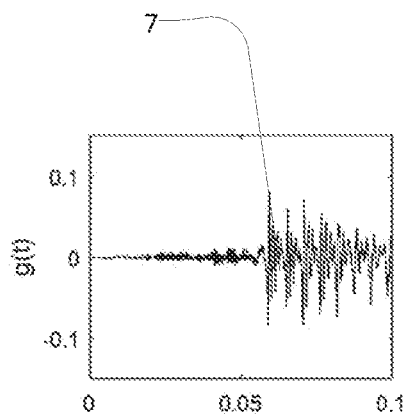
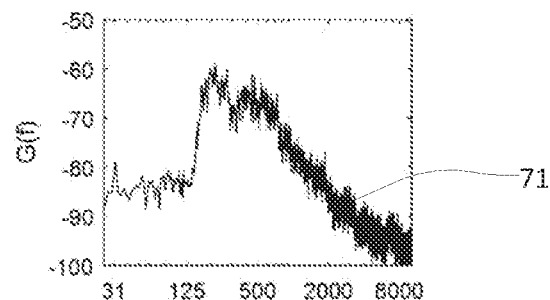
Fig. 5　　　　　Fig. 6
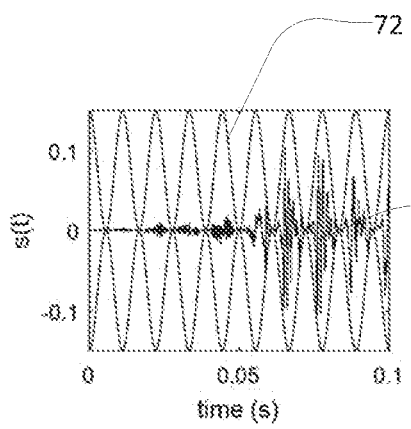
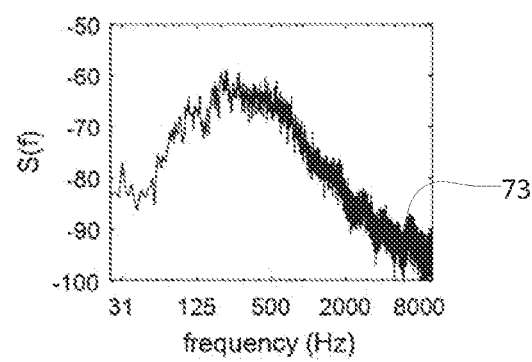
Fig. 7　　　　　Fig. 8

SYSTEM AND METHOD FOR VALIDATION OF HEARING AIDS FOR INFANTS USING A SPEECH SIGNAL

This application is a Continuation of copending U.S. application Ser. No. 16/457,364, filed on Jun. 28, 2019, which claims priority under 35 U.S.C. § 119(a) to Application No. 18180836.1, filed in Europe on Jun. 29, 2018, all of which are hereby expressly incorporated by reference into the present application.

FIELD

The present disclosure relates to a hearing diagnostic system, which is configured to perform an objective validation of a hearing aid performance by sound presentation to the ear of a test person when no active intentional responses can be obtained from the person under test. More specifically, the disclosures relate to a system comprising diagnostic devices, and methods which by a measure of auditory evoked responses from the scalp of a person enables a validation of the hearing aid performance in especially infants and young children.

BACKGROUND

When a child is diagnosed with a potential hearing loss from a hearing screening performed in an early stage after birth, the child is referred to further diagnostic testing to evaluate the cause of the hearing loss and the degree of the hearing loss present. Especially the degree of a hearing loss is important to evaluate, and tests have been developed to indicate the degree of hearing loss from a measure of neurological activity caused by hearing. One challenge is, that a small child, —be it normally hearing or one who has degraded or loss of hearing—cannot physically provide an answer as to whether he or she is able to hear a sound or not, and therefore an objective neurological test is performed instead. Such tests include among other tests measures of the brain activity related to hearing which are called evoked potentials, such as auditory brain responses (ABR) or auditory steady state responses (ASSR). In such tests, a stimulus designed to generate an auditory evoked response from the brain is transmitted into the ear of a child, and electrodes arranged on the scalp of the child record any brain response arising from the stimulus. From these responses, provided at different frequencies of hearing, the amount of hearing loss for each frequency can be assessed in an audiogram and a hearing aid may be programmed to compensate for the measured hearing loss indicated by the audiogram data. Other types of stimuli signals used for similar testing is the Cortical Auditory Evoked potential (CAEP) test. These signals are configured as several different speech sounds called phonemes, like 'm', 'g' and 't', which are presented through a loudspeaker at a range of levels. Evoked responses to the sounds are recorded from the surface of the head recorded via electrodes and analyzed on a computer. Thus, the CAEP test signals are merely signals including only phonemes, and is not configured as running speech. In more detail, a phonemes is short piece of speech, which in CAEP measurements are used as stimulus.

Upon having programmed the hearing aid to compensate for a measured hearing loss, the compensation provided by the hearing aid has to be verified and further validated to ensure that the hearing loss is correctly compensated for and that the child can actually hear relevant sounds played through the hearing aid. The verification process aims at providing an objective estimate of the sound that the hearing aid is producing in the ear of a person. This process is to ensure that the hearing aid is performing as intended and programmed. However, when it has been ensured that the hearing aid is performing as intended (e.g. meets the prescribed target gain etc.), it is subsequently necessary to perform a more subjective evaluation of whether the hearing aid performance actually also meets the needs of the hearing impaired person. This procedure is called validation. Traditionally, in this validation process the hearing impaired person actively has to provide an oral or other physical response to evaluate if a certain sound, level of sound, noise, etc. is meeting the needs for the hearing impaired (i.e. a "subjective evaluation"). Thus, when fitting children, especially infants or very small children these physical responses or reactions to a sound played into the ear of the child cannot be evaluated sufficiently, since the child might not be able to speak or articulate intentionally in response to the sounds played to the child. Accordingly, the effectiveness of the amplification settings should be evaluated by other means. For children, current methods rely on the understanding and active participation from the child, which cannot be granted considering younger children or infants.

Therefore, there is a need to provide for a system, method and tool, which enables an evaluation and validation of the "subjective" hearing performance of a hearing aid, when no subjective physical, oral, or active intentional response can be obtained from the test person, e.g. a small child with a hearing loss.

SUMMARY

The current disclosure provides a system, method, and tool which enables e.g. a hearing care professional to objectively validate the hearing aid performance for a child, when no active intentional responses can be expected from the child who is being treated for a hearing loss. The system is configured to perform a hearing test, wherein a validation mode is used to evaluate the hearing ability of a person, e.g. a small child, in the aided condition (i.e. when the child is wearing a hearing aid). In order to perform such objective evaluation, the system comprises one or more electrodes, which are configured to be arranged on the scalp of a person under test, and where the one or more electrodes are configured to be connected to a diagnostic device. It should be noted that the "person under test", the "hearing impaired" or other similar denotation of the test person in this context is mainly related to a small child, who is unable to provide an intentional physical response to a stimulus signal. However, it could also include other hearing impaired persons, who have difficulties in expressing themselves physically or orally. Similarly, "hearing aid" should be understood to be any hearing prosthetic device, including cochlear implants, bone-anchored hearing devices etc. In order to generate a stimulus signal used in the objective validation mode, the system furthermore comprises a sound emitting device, which is configured to be connected to the diagnostic device and to transmit a generated sound stimulus to the aided ear of a person.

Furthermore, the diagnostic device is configured to be set in at least a validation mode, and for transmitting a sound stimulus, recording and processing the response data received from the hearing test, the diagnostic tool comprises; a signal generator configured to transmit a generated stimulus to the sound emitting device; a recording processor configured to receive a response signal from the one or more electrodes arranged on the scalp of the person under test; and a control unit configured to control the mode of operation of the diagnostic device, wherein in the validation mode of operation, the signal generator is configured to generate the sound stimulus and to transmit the generated sound stimulus to the sound emitting device, wherein the generated sound stimulus is configured as an amplitude and/or frequency modulated naturally occurring sound.

In other words, a system including a diagnostic device and one or more electrodes configured to record an auditory evoked response from the brain of a person is provided for. The diagnostic device is configured to transmit a stimulus, which is generated from a naturally occurring sound. The naturally occurring sound is either input to the diagnostic tool or is already provided in a sound processor of the diagnostic tool, and the naturally occurring sound is amplitude and/or frequency modulated so as to create a frequency and/or amplitude modulated stimulus from a naturally occurring sound. By using such amplitude and/or frequency modulated naturally occurring sound it is possible to create a sound stimulus which is able to evoke auditory brain responses, while at the same time being not only "speech-like" but actually created from, e.g., a speech signal, and which thus is less distorted than the known types of speech-like stimuli that are used for detecting auditory evoked responses.

Accordingly, the definition of natural occurring sound should be construed as a sound existing naturally in the environment of humans, and which has not been processed by any machine, computer, processor or similar. In accordance herewith, natural means "existing in or formed by nature (as opposed to artificial)". Accordingly, the natural occurring sound could be a speech signal as spoken by a human person, birds singing, dogs barking, children playing, live music, piano music etc. In other words, the natural occurring sound is in case of speech to be construed as "running-speech", which is defined as the continuous sound of spoken dialogue from which the listener is able to distinguish individual words and sentences. Thus, the stimulus used in this setup is a preferred embodiment, a natural occurring sound, such as running speech, which is frequency and/or amplitude modulated. This stimulus is in contrast to e.g. CAEP (which are pieces of speech used as stimulus as previous explained), a stimulus containing running speech, and not only selected pieces (phonemes) of running speech.

It should be noted that in a preferred embodiment, the auditory evoked responses that are detected are auditory steady state responses (ASSR) or envelope-following responses (EFR).

In more detail, when the validation of the "subjective" performance of a hearing aid is assessed and no subjective physical, oral, or active intentional response can be obtained from the test person, e.g. a small child with a hearing loss, it is important that the test stimulus is sufficiently speech-like to be classified as speech by one or more hearing aids arranged behind the ears of the child. It should be noted that the applications described herein could similarly be used for in-the-ear type hearing aids. Regularly used auditory evoked-response stimuli are, when presented to the hearing aid, processed as noise by the hearing aid, and can therefore potentially lead to misleading results of the validation process. Instead, according to the disclosure, it has been found that providing a naturally occurring sound, such as speech, and generating a frequency and/or amplitude modulated version of this naturally occurring sound, an auditory evoked-response stimulus which is not considered as noise by the hearing aid can be generated. Thus, in the validation process of a hearing aid, such a stimulus is presented to the hearing aid, and comprises components of the stimulus signal which are not modified or removed from the stimulus by the hearing aid, which would have been the case for e.g. a standard chirp stimulus. Thus, by providing a frequency and/or amplitude modulated stimulus based on a naturally occurring signal, e.g. speech, in the validation step of the hearing aid test, it is possible to get an auditory evoked response from the brain of the test person, so as to objectively and correctly, in terms of hearing-aid gain and selection of signal-processing features, evaluate the "subjective" performance of the hearing aid.

It should be noted that in the following, the generated sound stimulus should be understood as being a sound stimulus which is purely based on a naturally occurring sound (refer to previous definition), preferably a speech signal, which has been amplitude and/or frequency modulated to create the necessary auditory evoking components in the signal.

For transmitting the generated stimulus based on a naturally occurring sound to the hearing aids, the sound emitting device may in an embodiment be configured as the one or more hearing aids, which are arranged on the ear or ears of the test person in the validation mode of the diagnostic device. Thus, in an embodiment the generated sound stimulus may be transmitted into the ear of a hearing-aid user directly via the hearing aids.

In a more preferred embodiment, the sound emitting device is configured as a loudspeaker. The loudspeaker is in this embodiment connected to the diagnostic device and is externally arranged in relation to the one or more hearing aids. By externally arranged should be construed that the loudspeaker is located in the ambient surrounds to the hearing aids. That is, the loudspeaker in this embodiment may be arranged in the "test room" at a distance away from the hearing aids arranged on the patient/child. The loudspeaker is configured to receive the generated sound stimulus from the signal generator and to play the generated sound stimuli to the one or more hearing aids arranged of the ears of a person. By presenting the sound stimulus to the hearing aid via a loudspeaker, it is ensured that the sound presented to the ear of the user is processed in the hearing aid in a regular way. Thus, the sound is presented to the ear of a user with the same hearing aid processing as used in daily life with real speech signals, and due to the fact that the sound stimulus is generated from a naturally occurring sound, the sound is not considered as noise by the hearing aid, and therefore transmitted substantially with all of the frequency content to the ear of a user and with the amplification adequate for real speech. The amplitude and/or frequency modulations applied to the naturally occurring sound then acts to evoke auditory brain responses, which may be recorded by the electrodes arranged on the scalp of the hearing-aid user.

The fact that the proposed stimulus is not only speech-like, but actually based on a naturally occurring signal, e.g. speech, has the additional advantage to underpin the face validity of the validation test towards both clinicians and the parents/caregivers of the child under test. Thus, in the validation mode, the diagnostic tool is configured to transmit the generated sound stimulus to the one or more hearing aids via the hearing aids or via the externally arranged loudspeaker, whereby the hearing aids presents the transmitted generated sound stimulus in the ear of the person, such that auditory evoked responses are generated and recorded by the electrodes arranged on the scalp. The recorded evoked responses are transmitted to the diagnostic device as auditory evoked responses (AER), such as auditory steady state responses (ASSR).

The naturally occurring sound which is processed with an amplitude and/or frequency modulation is preferably a sound recorded in the test environment of the child being tested. That is, in an embodiment, the sound stimulus is generated from a recording of the naturally occurring sound, which is input to the diagnostic device. That is, for example, a parent to a child may speak into an external microphone, whereby the speech of the parent is recorded and used as input to the sound stimulus generation. Thus, the naturally occurring sound is in an embodiment provided as speech from a human person, and the recorded naturally occurring sound is transmitted wired or wirelessly to the diagnostic device. In the diagnostic device, the sound stimulus generator processes the recorded human speech to generate an amplitude and/or frequency modulation of the recorded naturally occurring sound resulting in the sound stimulus which is transmitted to loudspeaker or directly to the hearing aids of the child under test, as described above. By enabling the possibility of recording speech from e.g. a parent, it is ensured that the child, that is being tested for a hearing loss and fitted with a hearing aid, is presented with the voice of e.g. the mother or father of the child, instead of a synthetically generated voice signal, which may be constructed from e.g. a plurality of different speakers' voices (e.g. the international speech test signal, (ISTS)). The ISTS signal is an internationally recognized test signal that may be used in the technical evaluation of hearing instruments, and for probe-microphone measurements. The ISTS is based on natural recordings of speech which is non-intelligible due to remixing and segmentation. Instead the voices that the child are presented with are as close to their normal daily life as possible, and at the same time the mother or father of the child can actually experience how their child is able to hear their voices during the validation test, and as the direct result of the hearing-aid fitting.

In another embodiment, the naturally occurring sound may be recorded via a computer or another external device and subsequently transmitted to the diagnostic tool. That is, the sound stimulus generation of the recorded naturally occurring sound, preferably a speech signal, may be performed in the diagnostic tool, but may also be performed in a device external to the diagnostic tool, such as in a computer, an app on a mobile phone or similar devices. Thus, independently of the medium on which the sound stimulus generation (processing of the recorded sound) takes place, the processing steps performed on the recorded naturally occurring signal are the same.

Thus, in an embodiment, the recorded naturally occurring sound is received in a sound signal generator (e.g. in the diagnostic tool or another medium capable of processing a signal), wherein the recorded naturally occurring sound is processed in the following steps; first the recorded naturally occurring sound is filtered into a plurality of frequency sub-bands; secondly, each of the plurality of frequency sub-bands are independently amplitude and/or frequency modulated; wherein in a third step the amplitude and/or frequency modulated sub-bands are combined to form the sound stimulus. Thus, the natural recorded sound, preferably a speech signal, is split into different frequency sub-bands to ensure that multiple narrower ranges of the entire frequency-range of hearing can be tested simultaneously by means of the sound stimulus. Thus, each of the bands are frequency and/or amplitude modulated to ensure that each of the sub-bands comprises components which are able to stimulate an auditory evoked response, preferably an auditory steady state response (ASSR).

In an alternatively preferred embodiment, the recorded naturally occurring sound is received in a sound signal generator (e.g. in the diagnostic tool or another medium capable of processing a signal), wherein the recorded naturally occurring sound is processed in the following steps; first the recorded naturally occurring sound is frequency or amplitude modulated with a plurality of modulator functions having different modulation rates;
    secondly each of the plurality of amplitude and/or frequency modulated recorded naturally occurring sounds is subsequently filtered by one of a plurality of frequency sub-bands chosen for each of the modulations of the recorded naturally occurring sound;
    wherein further the amplitude and/or frequency modulated sub-bands are combined to form said sound stimulus.

In more detail for each of the alternatives described above, the amplitude and/or frequency modulated frequency sub-bands may be adjusted in magnitude to align with a predetermined set of values. This is to ensure that the magnitude of the sub-bands is either in accordance with a desired test target level for each stimulus sub-band in question, or to ensure that the generated stimulus resembles a natural speech signal. The latter approach serves two purposes: 1) to further ensure that the hearing aid will process the stimulus as speech and not as noise, and 2) to ensure that the validation test actually is indicative of whether or not a real speech signal is audible when the hearing aid is used.

Accordingly, in an embodiment, the predetermined set of values is provided as a set of band powers of a standardized speech test signal at any of the frequency sub-bands or the predetermined set of values is provided as band powers of the recorded naturally occurring sound. It should be construed that the standardized speech test signal in an embodiment may be the international speech test signal (ISTS), or e.g. the ICRA 1-talker babble (ref. Wouter A. Dreschler, Hans Verschuure, Carl Ludvigsen & Søren Westermann (2001) ICRA Noises: Artificial Noise Signals with Speech-like Spectral and Temporal Properties for Hearing Instrument Assessment: Ruidos ICRA: Señates de ruido artificial con espectro similar al habla y propiedades temporales para pruebas de instrumentos auditivos, Audiology, 40:3, 148-157, DOI: 10.3109/00206090109073110). In this way, it may be ensured that the sound stimulus generated from the naturally occurring sound has adequate magnitude to resemble a normal speech signal, so as to cause an auditory evoked response representative of real speech input, while at the same time ensuring that the hearing aids will process the entire stimulus signal as speech and not as noise.

In any of the embodiments described above it should be noted that also a standardized speech signal can be used as the input signal to the signal generator.

Due to the frequency and/or amplitude modulation of the naturally occurring sound, being the recorded sound or e.g. the standardized speech signal, the signal may be somewhat distorted in comparison to a clean speech signal. However, to improve the speech content of the resulting stimulus, the processing step of generating the sound stimulus may include a further step of setting an amplitude and/or a frequency modulation factor for one or more of the plurality of sub-bands to 0, so as to leave the respective sub-band unmodified. This in effect ensures that the frequency and/or amplitude modulation does not affect the specific sub-band of which the speech content in full will be left unmodified.

This can be advantageous for enforcing the point that the stimulus is (very close to) real speech, which is a potentially important trait of the proposed validation method in terms of the counselling of the parents/caregivers of the child under test, as well as the clinician administering the validation test.

The system is configured such that the auditory evoked responses, preferably auditory steady state responses, can be detected from measurements by the electrodes arranged on the scalp of the test person, preferably a small child. The system is thus configured such that the diagnostic tool in the validation mode controls the transmission of the sound stimulus to the ears of the child via the hearing aids. The stimulus signal is transmitted continuously until a response is measured for all of the sub-band frequencies tested, or until the test is terminated on the grounds of futility (i.e. detection not expected even with prolonged testing). Accordingly, in an embodiment, the diagnostic tool is configured to control a first transmission, wherein the entire frequency band of the sound stimulus is played to the hearing aids. Upon detecting a response from the electrodes within a specified frequency sub-band, the specific frequency sub-band is turned off (i.e. set to 0) so as to remove the specific frequency sub-band for which a response is detected from the stimulus. This is done to minimize stimulus band interaction, or spread of excitation in the cochlea, that may hamper detection of the yet undetected frequency sub-bands. Thus, the remaining sub-band evoked responses may be detected faster. Thus, for every time a response from the electrodes is detected for a specified frequency, the respective sub-band accounting for this frequency is turned off, and the remaining frequency content of the stimulus signal is presented to the ears of the small child via the hearing aids.

In principle any frequency could be tested for in the described setup. However, the frequencies that are most interesting for characterizing hearing losses are the main focus of this application. Thus, in an embodiment, the naturally occurring sound may be band-pass filtered into four one-octave wide frequency sub-bands having center frequencies of 500 Hz, 1 kHz, 2 kHz, and 4 kHz.

Preferably each of the sub-bands may be amplitude and/or frequency modulated with modulator functions having different modulation rates for each of the sub-bands. This allows the auditory evoked responses from the respective stimulation sub-bands to be separated in the frequency domain.

In general, and as described in more detail herein, each of the modulator functions applied to generate the sound stimulus from the naturally occurring sound is preferably configured as a sinusoid.

Furthermore, the most interesting auditory evoked responses for this application is, as already implied, the auditory steady state responses, which is why the response signal recorded from the electrodes preferably is the auditory steady state responses (ASSR).

The embodiments of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each embodiment may each be combined with any or all features of the other embodiment.

BRIEF DESCRIPTION OF THE DRAWINGS

The embodiments, features and/or technical effect will be apparent from and elucidated with reference to the illustrations described hereinafter in which:

FIG. 5 illustrates an example of a speech signal in the time domain;

FIG. 6 illustrates a frequency spectrum of the speech signal of FIG. 5;

FIG. 7 illustrates a modulation function and the signal resulting from applying said modulation function to the speech signal of FIG. 5;

FIG. 8 illustrates a frequency spectrum of the modulated signal in FIG. 7;

DETAILED DESCRIPTION

Figure 1:
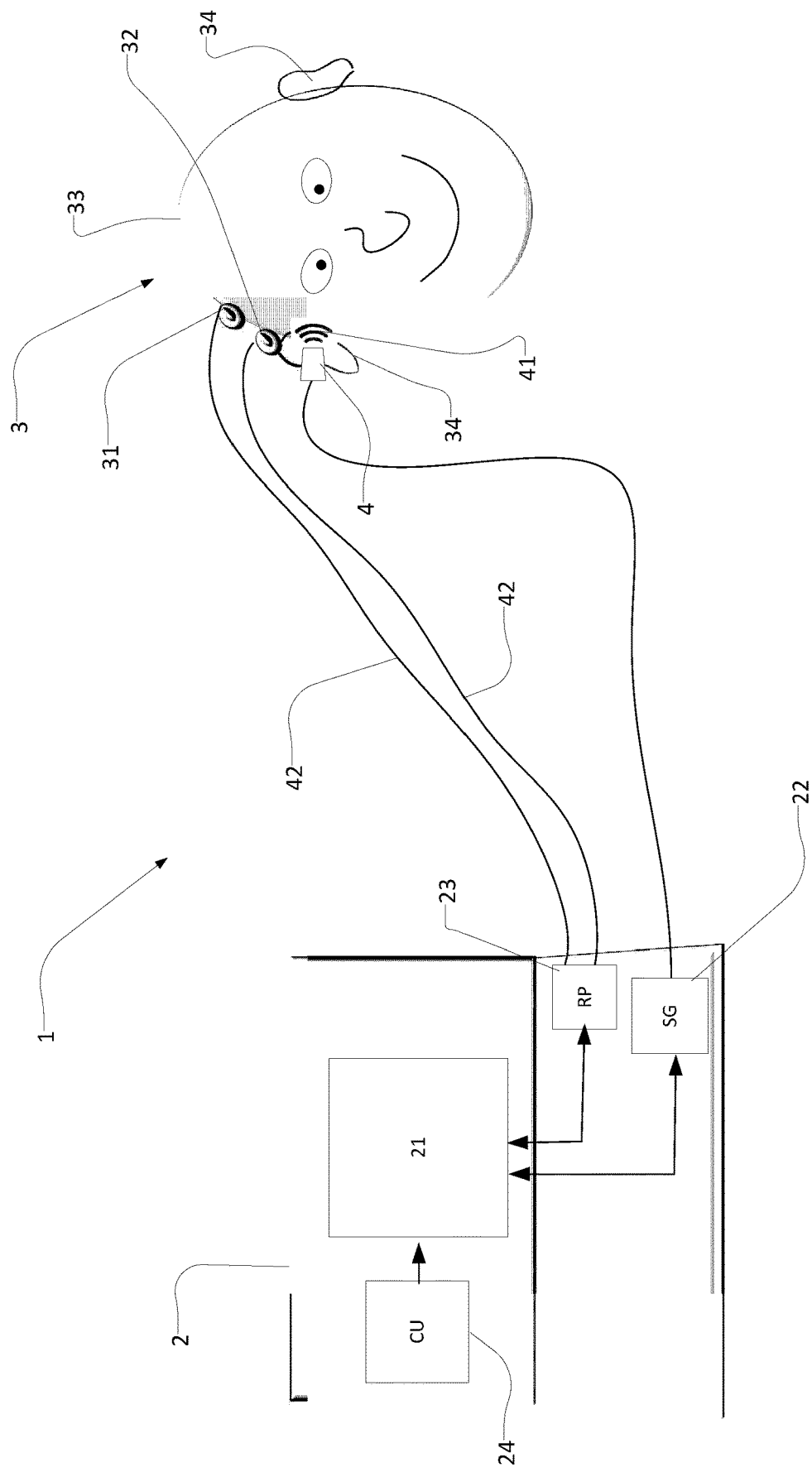
FIG. 1 illustrates various parts of the system according to an embodiment of the disclosure.

Referring initially to FIG. 1, an illustration of various parts of the system according to an embodiment of the disclosure is shown. As seen in FIG. 1, the system 1 comprises a diagnostic device 2, one or more electrodes 31, 32 and a sound emitting device 4. Furthermore, FIG. 1 illustrates the setup of the system 1 in a diagnostic validation mode, where a child 3 is presented with a sound stimulus via the sound emitting device 4, and has arranged on the scalp 33 the one or more electrodes 31, 32, so that the system may perform a hearing test, especially a validation test to evaluate the performance of a hearing aid ability to compensate for the hearing impairment of the child.

As illustrated, the one or more electrodes 31, 32 are configured to be arranged on the scalp 33 of the child 3 (or other hearing impaired test person) under test and are configured to be connected to the diagnostic device 2 (e.g. via wires 42 or alternatively in a wireless manner). In the embodiment shown in FIG. 1, the sound emitting device 4 is configured as a probe which is connected to the diagnostic device 2 and is configured to transmit a sound stimulus 41 into the ear of the child 3. The sound stimulus 41 may as will be apparent in the following description of the embodiments be generated in the diagnostic device 2 or externally thereto.

The diagnostic tool 2 is in more detail configured to be set in at least a validation mode. Thus, the diagnostic tool 2 may comprise a control unit 24 configured to control one or more modes of operation, but for this application the validation mode is considered in more detail in light of validating the performance of the hearing aid after having fitted the hearing aid to e.g. a child. Furthermore, the diagnostic tool comprises a signal generator (SG) 22, which is configured to transmit the generated stimulus to the sound emitting device 4. For recording the obtained responses from the electrodes 31, 32 arranged on the scalp 33 of the child 3, the diagnostic device is configured with a recording processor (RP) 23, which takes as input the responses obtained by the electrodes 31, 32. Accordingly, the diagnostic tool 2 is configured to be controlled by a user, e.g. a hearing care professional, a doctor or other professional who has the intention of testing, screening, and most relevant for this application to validate a hearing aid fitting to e.g. a hearing impaired small child. As will become apparent the diagnostic tool is when controlled into a validation mode configured to cause the signal generator 22 to generate a sound stimulus and to transmit the generated sound stimulus to the sound emitting device 4, wherein the generated sound stimulus is configured as an amplitude and/or frequency modulated naturally occurring sound.

Figure 2:
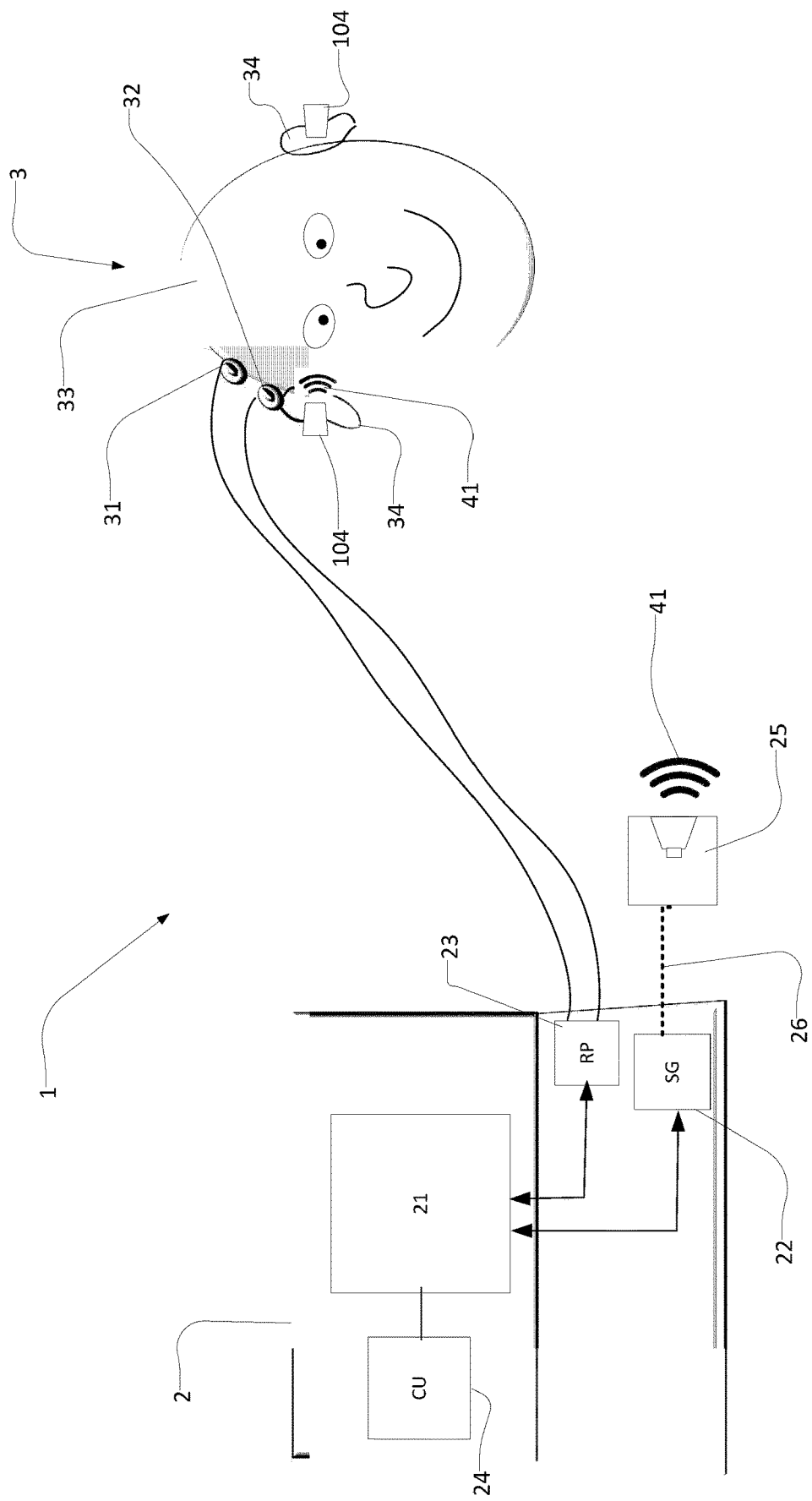
FIG. 2 illustrates parts of the system according to an embodiment of the disclosure.

Several notes should be mentioned here. First, it should be noted that the sound stimulus may be generated in the diagnostic tool, but may also be generated externally thereto. Secondly, the sound emitting device may be a probe as illustrated schematically in FIG. 1, but could similarly be a loudspeaker as illustrated in FIG. 2. In addition, it should be noted that the sound emitted to the ear should preferably undergo a processing scheme corresponding to the processing performed by a hearing aid before the sound is presented to the ear. Thus in a preferred in embodiment, the child under test should have hearing aids arranged on the ears, and sound should be emitted to the ear via the hearings aids. When sound is presented via a loudspeaker, one ear is tested at a time, and the non-tested ear should be plugged, e.g. with a foam ear-plug.

In general, with a system as described herein, the hearing aid performance can be evaluated for a child having a hearing impairment and who is unable to provide a response to a signal transmitted to the ear of the child. Thus, this objective validation setup provided by the system allows a stimulus which when processed by the hearing aid is not considered as noise and does activate the brain of the child in such manner that the electrodes can record the auditory steady state responses, which the stimulus evoke. It should be noted that current validation methods merely rely on the face changes, noises or similar spontaneous physical changes that the child expresses when being presented with different stimuli, while this system and method allows an objective evaluation of the performance of the hearing aid, rather than the subjective evaluation based on e.g. facial expressions from the child under test.

In the following, different system setups will be explained in more detail and finally the method of generating the sound stimulus which may be based on a naturally occurring sound, preferably speech, will be described. It should be noted that corresponding features for each embodiment will have the same number adhered thereto in the following description of various embodiments.

Referring now to FIG. 2, a preferred setup for the system is described. Here the setup is more or less as described in relation to the embodiment of FIG. 1, wherein the differences lies in that the sound emitting device is configured as a loudspeaker 25, which is connected either wired or wirelessly 26 to the diagnostic tool 2 and emits the generated sound stimulus 41. In this embodiment, the child 3 is wearing the hearing aid (or hearing aids) 104, of which the performance should be evaluated. In the setup according to FIG. 2, it is preferred that only one ear is tested at a time, while the second ear is plugged, as already explained above.

Accordingly, in this setup, the diagnostic tool 2 is set in the validation mode 21 via the control unit 24 and configured to generate a sound stimulus, which is configured as an amplitude and/or frequency modulated naturally occurring signal. The generated stimulus is transmitted wirelessly or wired to the loudspeaker 25, which emits the sound stimulus 41. The emitted sound stimulus is picked up by the hearing aid 104, which processes the sound stimulus in a regular manner in accordance with the hearing aid settings, and then emits the sound stimulus into the ear 34 of the child 3.

The emitted sound stimulus evokes a brain response known as the auditory steady state response (ASSR), which is picked up by the electrodes 31, 32 arranged on the scalp 33 of the child 3. The ASSR signals picked up by the electrodes 31, 32 is transmitted to the diagnostic device 2 wherein a detection scheme is used to detect if a response is present or not. The important note here, and for all of the other embodiments described, is that the sound stimulus is processed by the hearing aid in a similar manner as normal speech, while at the same time being able to evoke the ASSR.

Figure 3:
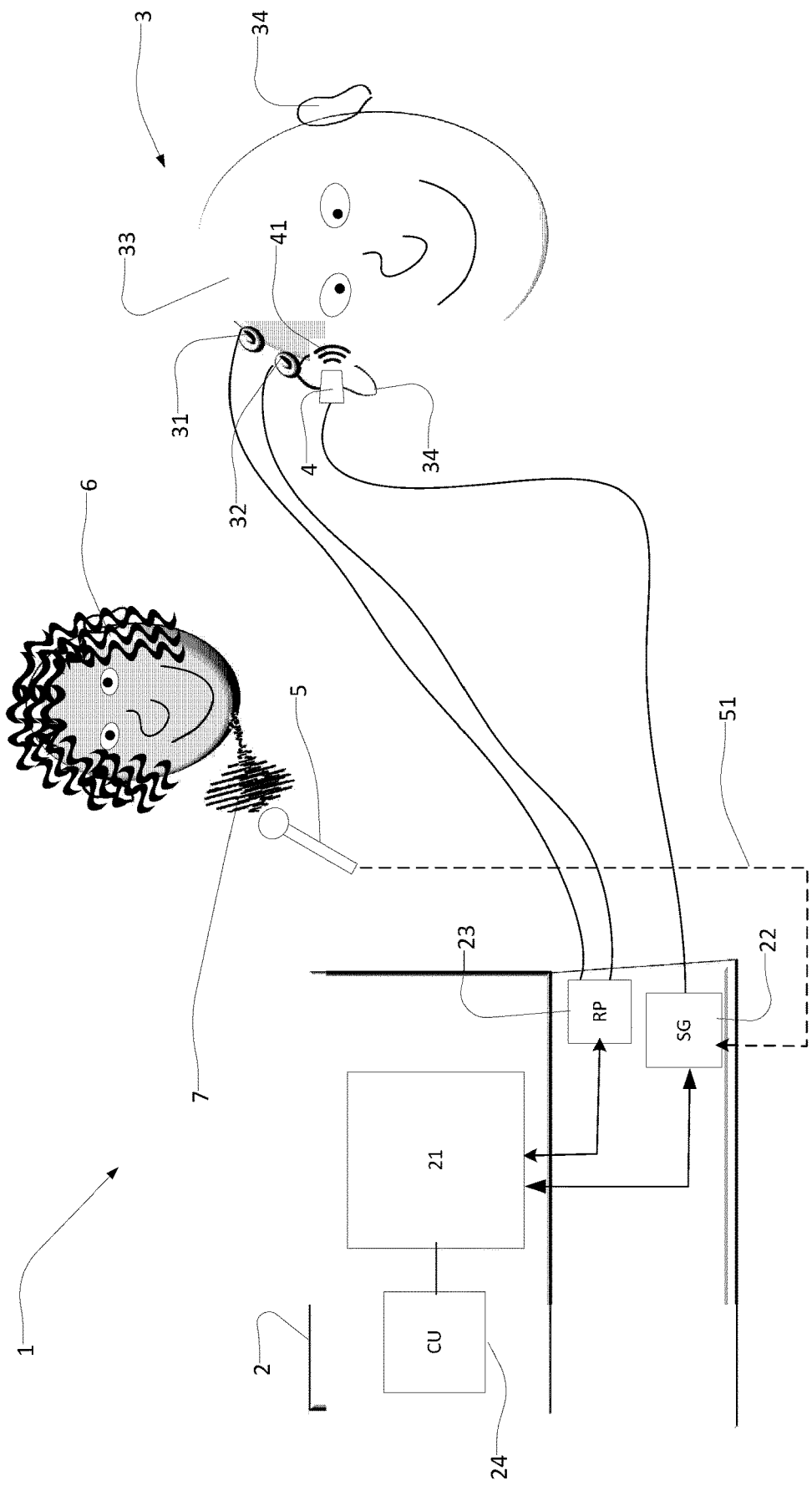
FIG. 3 illustrates various parts of the system according to FIG. 1, wherein the naturally occurring sound is recorded as speech from e.g. a mother to a child.
Figure 4:
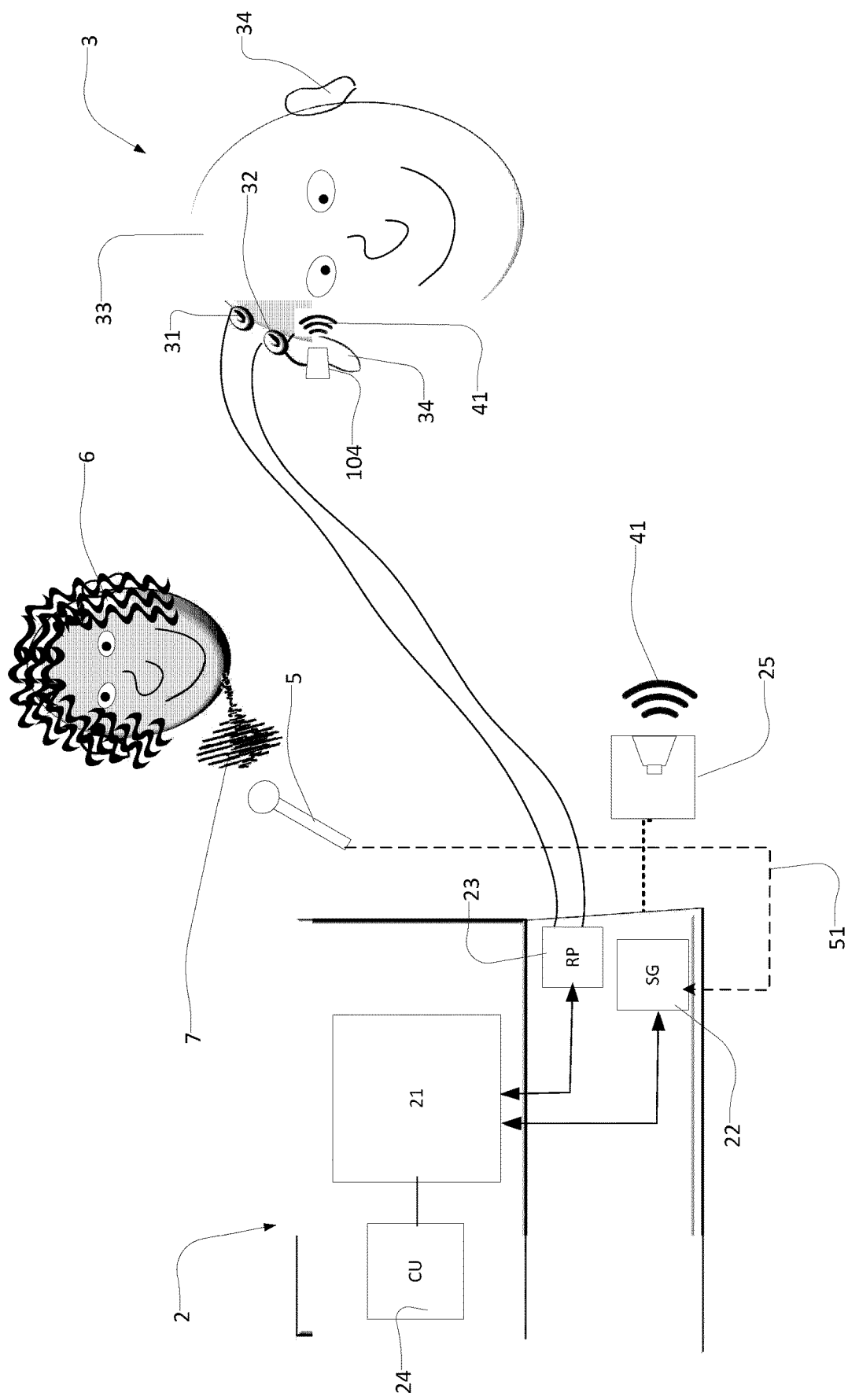
FIG. 4 illustrates various parts of the system according to FIG. 2, wherein the naturally occurring sound is recorded as a speech from e.g. a mother to a child.

In another embodiment illustrated in FIG. 3, most of the features described in the previous embodiments are present and the respective numbers adheres thereto. In FIG. 3 an embodiment, wherein the sound stimulus is generated from a recording of a naturally occurring sound is illustrated. Here the naturally occurring sound is configured as a speech signal 7 which is recorded via a recording device 5. The recorded speech signal 7 is input to the diagnostic device 2 via e.g. a transmission line 51, such as a wired or wireless transmission. In the diagnostic device 2, the recorded speech signal 7 is input to the sound stimulus generator 22, wherein the sound stimulus generator 22 generates an amplitude and/or frequency modulation of the speech. This creates the sound stimulus 41 which is delivered to the child 3 via a probe as illustrated in FIG. 3 or preferably via a loudspeaker 25 and a hearing aid 104, as illustrated in the embodiment of FIG. 4. By providing a system setup, where e.g. a parent's voice, such as the voice of the mother, can be recorded, processed, and used as frequency and/or amplitude modulated stimulus signal, it is ensured that the child 3 from early stages on hears a known voice and at the same time the parents will actually experience that their child is able to hear their voices.

As implied, the embodiment of FIG. 4 illustrates a similar setup as described in relation to FIG. 3. However, in the embodiment of FIG. 4, the sound stimulus 41 is presented to the hearing aid 104 via a loudspeaker, as also described in relation to FIG. 2. Thus in this system setup, the parent 6 (illustrated as a mother) provides a speech signal 7 which is recorded by a microphone 5. The signal is transmitted 51, either wired or wirelessly to the diagnostic device 2, wherein in the diagnostic device a sound stimulus generator 22 generates the sound stimulus 41 used to evoke the brain responses, such as the auditory steady state responses. The remaining processes are similar to what has been described in the previous embodiments, and will therefore not be elaborated on in further detail. As also described in relation to the embodiment of FIG. 2, it is in this setup preferred that only one ear is tested at a time, while the second ear is plugged.

It should be noted that for each of the system setups described in the above embodiments, the diagnostic device is illustrated schematically as a computer. However, this should not be limiting to the understanding that the diagnostic device could similarly be constituted by a dedicated hand-held or table-top diagnostic device, which has the same features incorporated therein.

In addition, the naturally occurring sound used for generating the sound stimulus evoking ASSR signals, could be a standardized speech signal, which is stored in a memory in the diagnostic device 2.

In another note, in case of e.g. a recorded speech signal, as described in relation to FIGS. 2 and 4, it should be noted that this recorded speech signal could be processed in an auxiliary device to the diagnostic tool, and then input to a memory or the signal generator of the diagnostic device after having undergone the needed processing (to be explained in the following) to be able to create a naturally occurring speech signal, which has features enabling the speech stimulus to evoke ASSR signals in the brain without being classified as noise by a hearing aid.

Until now the system set up in a diagnostic validation mode of the system has been explained in detail. In the following, the actual processing of the naturally occurring sound needed to generate a naturally occurring sound, preferably speech, which can be used as an ASSR evoking stimulus, will be explained in detail.

Referring initially to FIGS. 5 and 6, a time series of a naturally occurring sound, such as speech 7, is illustrated together with the frequency spectrum 71 thereof. Such speech signals are preferably used in the system described herein, since speech is most relevant for hearing. Accordingly, the speech signal illustrated in FIG. 5 could e.g. be a recorded speech signal as illustrated in FIGS. 2 and 4. Alternatively it could be a standardized speech signal, which e.g. is stored in the diagnostic device.

In FIG. 7 it is illustrated how an amplitude modulation of the speech signal may take place. That is, an ASSR-evoking stimulus may be generated from a speech signal g(t) by multiplying the speech signal g(t) with a sinusoidal amplitude modulation 72 to create a stimulus as given in equation 1

$$s(t) = [1 + \cos(2\pi f_R t)] \cdot g(t), \quad (1)$$

where $f_R$ is the 'repetition rate' or modulation frequency, e.g. 90 Hz. In the frequency domain this corresponds to equation 2, and the illustration shown in FIG. 8, $$S(f) = G(f) + 1/2[G(f - f_R) + G(f + f_R)], \quad (2)$$

where S and G are the spectra of s and g, respectively, and f is frequency. In this example, the speech signal 73 is amplitude modulated over the entire frequency range of the speech signal.

Figure 9:
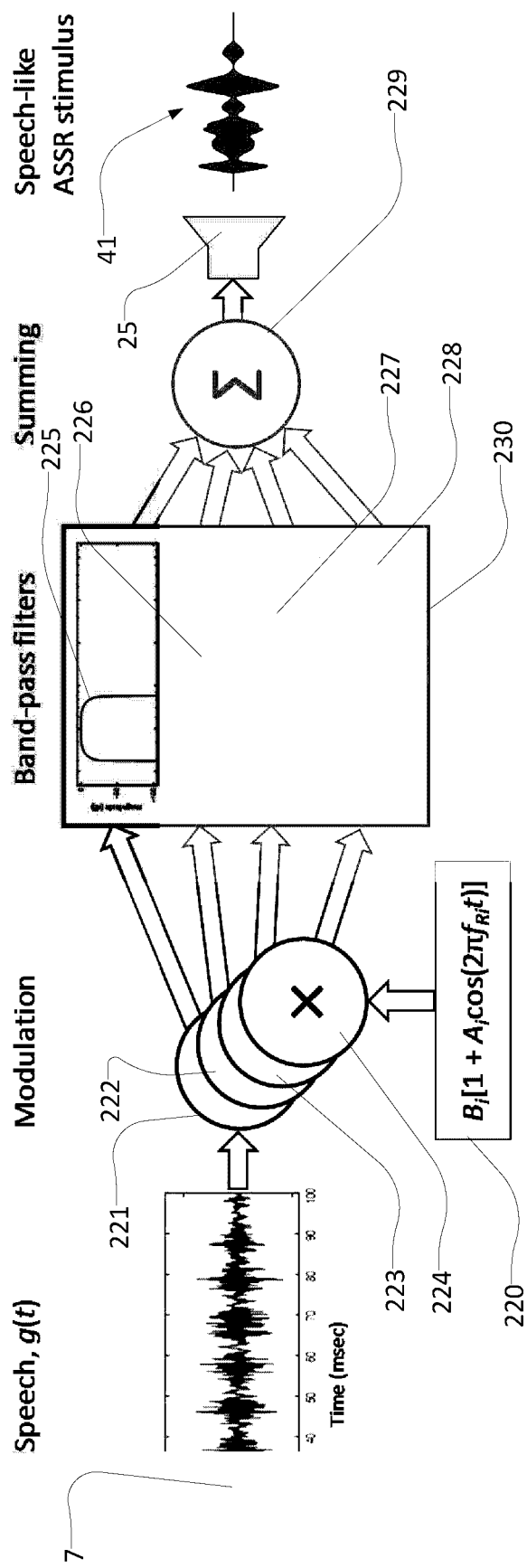
FIG. 9 illustrates schematically a preferred embodiment of the method of generating the ASSR speech stimulus.
Figure 10:
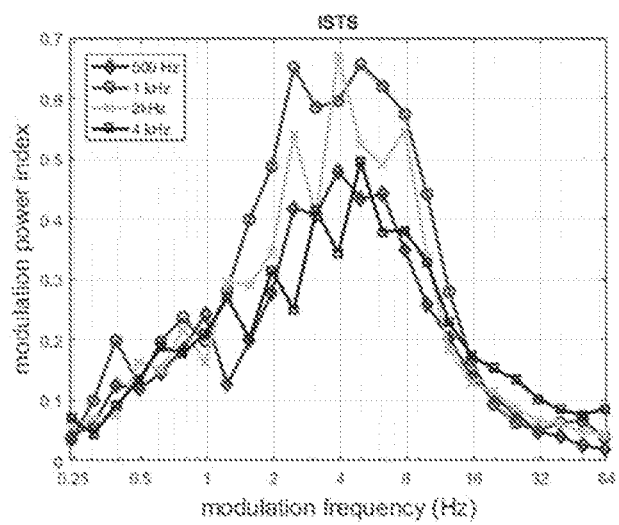
FIG. 10 illustrates example modulation powers of band-pass filtered versions of an international standardized speech signal.
Figure 11:
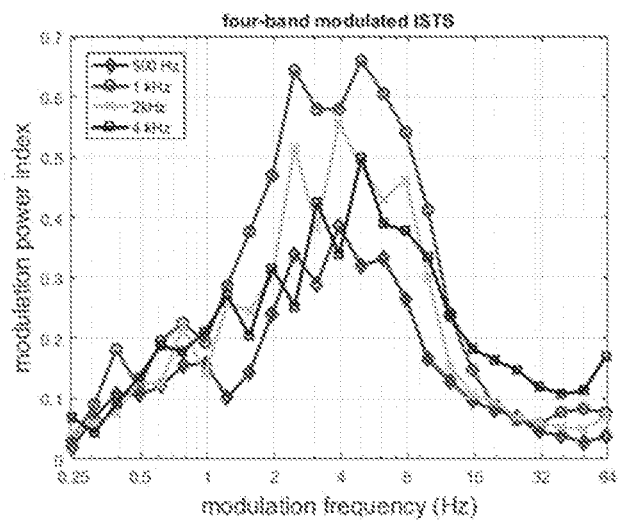
FIG. 11 illustrates example modulation powers of band-pass filtered versions of a four-band modulated international standardized speech signal.

However, in a preferred embodiment, the speech signal (i.e. the naturally occurring sound) is received in the sound signal generator (either from a recording of the speech or e.g. from a memory as previous described). Generally speaking, for all of the described embodiments, it should be understood that the speech signal (i.e. the naturally occurring signal) is modified as illustrated in FIG. 9, to become an ASSR stimulus. The amplitude and/or frequency modulation of the natural occurring sound may be performed in two alternative ways.

In a preferred first alternative, illustrated in FIG. 9, the sound stimulus 41 is generated in the sound signal generator in the following steps:

First the recorded naturally occurring sound (such as speech 7) is frequency or amplitude modulated 220 with a plurality of modulator functions 221, 222, 223, 224 having different modulation rates;

Secondly each of the plurality of amplitude and/or frequency modulated recorded naturally occurring sounds 221, 222, 223, 224 is filtered by one of a plurality of band-pass filters 225, 226, 227, 228 chosen for each of the modulations 221, 222, 223, 224 of the recorded naturally occurring sound; wherein further the amplitude and/or frequency modulated sub-bands are combined 229 to form said sound stimulus 41.

In more detail, in relation to the system setup, the recorded speech signal 7 is input to the signal generator 22 (refer to other embodiments described). In the signal generator, the speech signal 7 is amplitude or frequency modulated 220 with e.g. 4 modulator functions 221, 222, 223, 224, having different modulation rates. This ensures that the recorded auditory evoked responses respective to the different stimulation sub-bands (to be described) can be separated in the frequency domain. When the speech signal 7 has been modulated by e.g. 4 modulator functions 221, 222, 223, 224 as illustrated in FIG. 9, each of the 4 modulated speech signals are input to a filtering process 230. In this filtering process, a specific band-pass filter 225, 226, 227, 228 is chosen for each of the individual modulated speech signals 221, 222, 223, 224. This ensures that 4 sub-bands of the modulated speech signal is generated for the purpose of testing hearing ability in corresponding specific frequency ranges. The sub-bands are subsequently summed 229 (i.e. combined) to create the speech ASSR stimulus used for detecting ASSRs in the described setup. As described previously, the thus created speech ASSR stimulus is transmitted to the ear, preferably via a hearing aid, by a speaker, such as a loudspeaker, ad described in relation to FIGS. 2 and 4.

In a second alternative manner (not illustrated in more detail), the naturally occurring sound (i.e. speech) is in the sound signal generator processed in the following steps:

First the speech signal is filtered into a plurality of frequency sub-bands by means of a plurality of corresponding bandpass filters.

Secondly, the plurality of frequency sub-bands are amplitude and/or frequency modulated. That is, each of the sub-bands are amplitude and/or frequency modulated. This creates different frequency or amplitude modulated sub-bands of the speech signal, which in a final step are combined to form the sound stimulus.

For the preferred first alternative the frequency-specific embodiment of the invention can be devised by $$s(t) = \sum_{i=1}^{I} h_{BPi} * [(1 + A_i \cos(2\pi f_{Ri} t)) g(t)]$$

where g(t) is the naturally occurring signal, preferably speech, $h_{BPi}(t)$ are impulse responses of I band-pass filters, * denotes convolution, $f_{Ri}$ are the I different modulation frequencies, and $A_i$ are the I modulation depths.

For the second alternative, a frequency-specific embodiment of the invention can be devised by separating the speech signal into I sub-bands $g_i(t)=h_{BPi}(t)*g(t)$ and imposing amplitude modulations independently at different repetition rates for each sub-band, e.g.

$$s(t) = \sum_{i=1}^{I}(1 + A_i\cos(2\pi f_{Ri}t))g_i(t)$$

It should be noted that different modulation patterns may be created by adding more sidebands to the frequency modulated speech signal S(f) in the frequency domain, or by using different modulator functions in the time domain, e.g. $[1+A\cdot\cos(2\pi f_R t)]^N$, where $0<A\leq1$ and $N>0$, to create a more shallow or more peaky modulation pattern.

In order to ensure that the generated sound stimulus is sufficiently close to the original speech signal after having been processed with the frequency and/or amplitude modulations of the frequency sub-bands the amplitude and/or frequency modulated stimulus is adjusted in magnitude to align with a set of predetermined values. This is preferably done by adjusting the level of each bandpass filtered component of the combined stimulus, as shown below for the two aforementioned alternatives, respectively.

$$s(t) = \sum_{i=1}^{I} B_i h_{BPi} * [(1 + A_i\cos(2\pi f_{Ri}t))g(t)]$$

$$s(t) = \sum_{i=1}^{I} B_i(1 + A_i\cos(2\pi f_{Ri}t))g_i(t)$$

Figure 12:
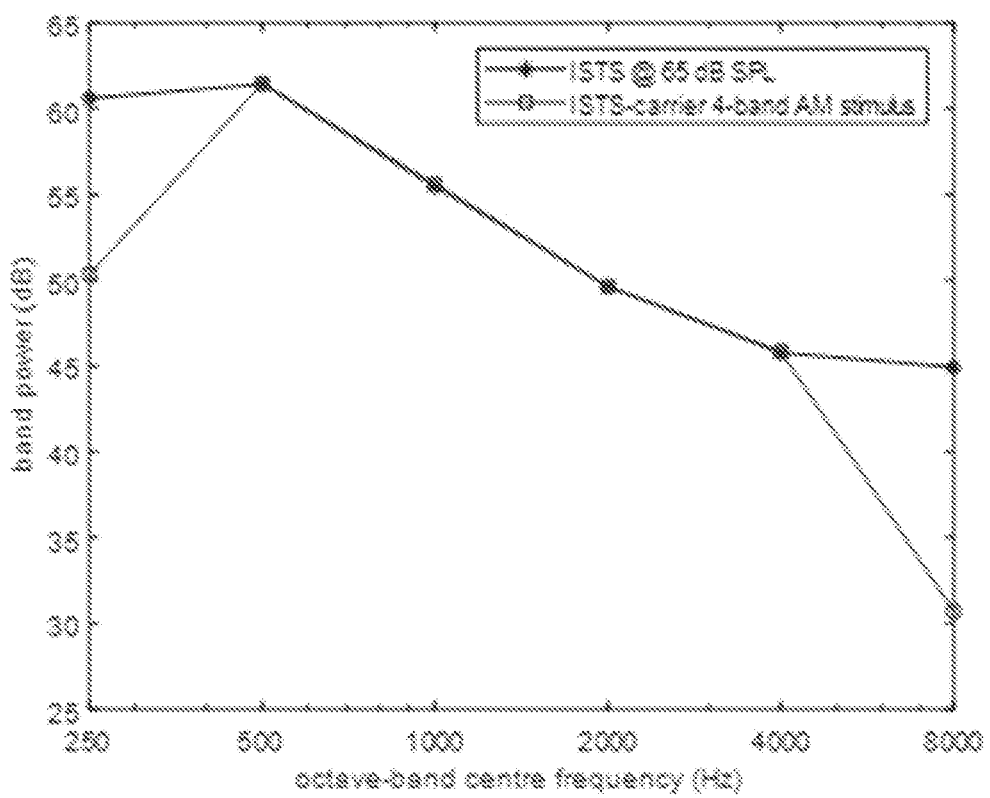
FIG. 12 illustrates the long-term one-octave power spectra of an international standardized speech signal, as well as a four-band modulated international standardized speech signal, after adjusting the amplitude of each of the four component bands.

Here, the values $B_i$, i=1, ..., I are the aforementioned set of predetermined values. As an example, FIG. 12 shows the long-term one-octave power spectra of an international standardized speech signal, as well as a four-band modulated international standardized speech signal, after adjusting the amplitude $B_i$, i=1, ..., 4 of each of the four component bands to obtain a match between the two one-octave band spectra.

Similarly, but not illustrated, a modulated modified naturally occurring speech signal may be adjusted in band-power so as to ensure that the speech content corresponds to the actual unmodified recorded speech signal.

The advantage of the amplitude-modulated speech signal (such as the ISTS signal) over previously known signals is that it maintains important characteristics of speech, which are crucial for a hearing aid's classification algorithms. One of the most important characteristics of speech used for signal classification in a hearing aid is the modulation power. The modulation power spectrum is determined by estimating the envelope of a signal and taking the Fourier transform of the envelope. As an exemplification of how the disclosed method preserves the modulation power structure of a speech signal, the illustrations in FIGS. 13 and 14 are provided. FIGS. 13 and 14 displays the modulation spectra computed in ⅓-octave wide frequency bands, for both the original ISTS and a four-band modulated ISTS. For the latter, the ISTS was filtered into four 1-octave wide frequency bands centered at 500 Hz, 1 kHz, 2 kHz, and 4 kHz, each of which were 100% amplitude modulated at 90.82 Hz, 97.66 Hz, 88.87 Hz, and 92.77 Hz, respectively. The results in FIGS. 13 and 14 show only minute changes to the modulation spectra between the original ISTS and the four-band modulated ISTS. The sound quality of the original speech (or any other carrier signal) is affected by the amplitude modulation, but the stimulus is easily recognized.

In a further step of the stimulus generation, it should be noted that one or more sub-bands could be left unmodified whereby a more natural sound quality of the speech signal is maintained. Thus in a processing step an amplitude and/or frequency modulation factor for one or more of said plurality of sub-bands is set to 0, so as to leave said respective sub-band unmodified.

It should be noted, that upon detecting a response, the specific frequency sub-band for which a response is detected is in an embodiment set to 0 (i.e. turned off), so as to remove the specific frequency band for which the response is detected form the stimulus. This allow a stronger contribution from the un-detected frequency sub-bands in the sound stimulus, and potentially a faster detection rate for the remaining plurality of frequency sub-bands. Thus, the stimulus is presented to the ears of a child until all the necessary responses has been detected to evaluate the entire hearing range.

In summary, it should now be clear that the inventors have come up with a way of validating the performance of hearing aids in an objective manner, by using a e.g. a naturally occurring and/or recorded speech signal, which has been modulated in order to create an ASSR evoking speech stimulus which is not considered as noise by a hearing aid.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A method for performing a validation mode of a hearing test for a person incapable of providing active intentional responses, said method comprising:

arranging one or more electrodes on the scalp of the person;

recording and/or receiving a recording of a naturally occurring sound provided as naturally occurring speech from a human person;

generating from said recording of the natural occurring sound, an amplitude and/or frequency modulation of said recording as a generated sound stimulus by filtering said recording of the naturally occurring sound into a plurality of frequency sub-bands, amplitude and/or frequency modulating each of said plurality of frequency sub-bands, where an amplitude and/or frequency modulation factor for one or more of said plurality of sub-bands is set to 0, so as to leave said respective sub-band unmodified when generating said sound stimulus, and combining said amplitude and/or frequency modulated sub-bands to form said sound stimulus;

transmitting the generated sound stimulus into the ear of the person; and receiving a response signal from said one or more electrodes.

2. The method according to claim 1, wherein said generated sound stimulus is transmitted to one or more hearing aids configured to be arranged on the ear or ears of said person during said validation mode of operation.

3. The method according to claim 2, further comprising: recording said response from said one or more electrodes arranged on said scalp of the person, wherein said response is provided as auditory evoked responses (AER).

4. The method according to claim 1, wherein said generated sound stimulus is transmitted to an external loudspeaker, which is arranged in the ambient surroundings to one or more hearing aids, wherein the external loudspeaker is configured to receive said generated stimulus and to play said generated sound stimulus to said one or more hearing aids configured to be arranged on the ears of a person.

5. The method according to claim 1, wherein said amplitude and/or frequency modulating each of said plurality of frequency sub-bands includes processing said recording of the naturally occurring sound by a frequency or amplitude modulation with a plurality of modulator functions having different modulation rates; and subsequently filtering each of said plurality of amplitude and/or frequency modulated recorded naturally occurring sounds by one of a plurality of frequency sub-bands chosen for each of the modulations of the recording of the naturally occurring sound.

6. The method according to claim 1, wherein each of said amplitude and/or frequency modulated frequency sub-bands are adjusted in magnitude to align with a predetermined set of values.

7. The method according to claim 6, wherein said predetermined set of values is provided as a set of band powers of a standardized Speech Test Signal at any of said frequency sub-band or said predetermined set of values is provided as band powers of said recording of the naturally occurring sound.

8. The method according to claim 1, wherein said naturally occurring sound may be a standardized speech signal.

9. The method according to claim 1, wherein the naturally occurring sound is band pass filtered into at least 4 frequency bands having center frequencies of 500 Hz, 1 kHz, 2 kHz, and 4 kHz.

10. The method according to claim 1, wherein each of said sub-bands are amplitude and/or frequency modulated with modulator functions having different modulation rates for each of said sub-bands.

11. The method according to claim 10, wherein said modulator functions are configured as a sinusoid.

12. A diagnostic device configured to perform at least a validation mode of a hearing test for a person incapable of providing active intentional responses, said diagnostic device comprising:

a recording processor configured to receive a response signal from one or more electrodes arranged on the scalp of the person;

a control unit configured to control the mode of operation of said diagnostic device; and a signal generator configured to transmit a generated stimulus to said sound emitting device, wherein, in a validation mode of operation said diagnostic device is configured to record and/or receive a recording of a naturally occurring sound provided as naturally occurring speech from a human person, input said recording of the natural occurring sound to said signal generator to generate a sound stimulus, and transmit the generated sound stimulus into the ear of the person;

wherein said signal generator is configured to generate from said recording of the natural occurring sound, an amplitude and/or frequency modulation of said recording as said generated sound stimulus by filtering said recording of the naturally occurring sound into a plurality of frequency sub-bands, amplitude and/or frequency modulating each of said plurality of frequency sub-bands, where an amplitude and/or frequency modulation factor for one or more of said plurality of sub-bands is set to 0, so as to leave said respective sub-band unmodified when generating said sound stimulus, and combining said amplitude and/or frequency modulated sub-bands to form said sound stimulus.

13. The device according to claim 12, wherein said generated sound stimulus is transmitted to one or more hearing aids configured to be arranged on the ear or ears of said person during said validation mode of operation.

14. The device according to claim 12, wherein said generated sound stimulus is transmitted to an external loudspeaker, which is arranged in the ambient surroundings to one or more hearing aids.

15. The device according to claim 12, wherein said amplitude and/or frequency modulating each of said plurality of frequency sub-bands includes processing said recording of the naturally occurring sound by a frequency or amplitude modulation with a plurality of modulator functions having different modulation rates; and subsequently filtering each of said plurality of amplitude and/or frequency modulated recorded naturally occurring sounds by one of a plurality of frequency sub-bands chosen for each of the modulations of the recording of the naturally occurring sound.

16. The device according to claim 15, wherein said modulator functions are configured as a sinusoid.

17. The device according to claim 12, wherein each of said amplitude and/or frequency modulated frequency sub-bands are adjusted in magnitude to align with a predetermined set of values.

18. The device according to claim 17, wherein said predetermined set of values is provided as a set of band powers of a standardized Speech Test Signal at any of said frequency sub-band or said predetermined set of values is provided as band powers of said recording of the naturally occurring sound.

19. The device according to claim 12, wherein said naturally occurring sound may be a standardized speech signal.

20. The device according to claim 12, wherein the naturally occurring sound is band pass filtered into at least 4 frequency bands having center frequencies of 500 Hz, 1 kHz, 2 kHz, and 4 kHz.

21. The device according to claim 12, wherein each of said sub-bands are amplitude and/or frequency modulated with modulator functions having different modulation rates for each of said sub-bands.

\* \* \* \* \*